United States Patent

Ramus

[11] 4,236,349
[45] Dec. 2, 1980

[54] ALGAE BIOPOLYMER PRODUCTION

[75] Inventor: Joseph S. Ramus, Gloucester, N.C.

[73] Assignee: Mobil Oil Corporation, New York, N.Y.

[21] Appl. No.: 927,698

[22] Filed: Jul. 24, 1978

[51] Int. Cl.³ .......................................... A01G 7/00
[52] U.S. Cl. .................................................... 47/1.4
[58] Field of Search ........................................ 47/1.4

[56] References Cited

U.S. PATENT DOCUMENTS

| | | | |
|---|---|---|---|
| 2,658,310 | 11/1953 | Cook | 47/1.4 |
| 2,732,662 | 1/1956 | Myers et al. | 47/1.4 |
| 3,224,143 | 12/1965 | Tew et al. | 47/1.4 |
| 3,504,185 | 3/1970 | Zweig et al. | 47/1.4 X |
| 3,958,364 | 5/1976 | Schenck et al. | 47/1.4 |
| 4,078,331 | 3/1978 | Savins et al. | 47/1.4 |
| 4,078,332 | 3/1978 | Savins | 47/1.4 |
| 4,079,544 | 3/1978 | Savins | 47/1.4 |
| 4,087,936 | 5/1978 | Savins et al. | 47/1.4 |

OTHER PUBLICATIONS

Photosynthesis of Amino Acids, Bassham et al., Biochim. Biophys. Acta, 90 (1964), pp. 553–562.

Primary Examiner—Robert E. Bagwill
Attorney, Agent, or Firm—C. A. Huggett; William D. Jackson

[57] ABSTRACT

Process and apparatus for the production of algae biopolymer employing a first stage for the growth of algae and a second stage for biopolymer production. In the first stage, growth of algae biomass in a culture medium is accomplished by operating the first stage in a continuous mode in which fresh nitrogen-containing nutrient medium is supplied to the culture. Concomitantly with the supply of fresh nutrient medium to the culture in the first stage, a portion of the culture medium is transferred from the first stage to the second stage in which the supply of nitrogen is limited. A nitrogen deficiency is created in the second stage to shift the culture to a senescent phase to enhance biopolymer production. The growth phase is carried out in a first stage reaction chamber which is connected to a plurality of second stage reaction chambers in parallel with one another. Culture withdrawn from the first stage is transferred sequentially to each of the second stage reaction chambers such that biopolymer production occurs in several second stage chambers simultaneously with cells produced in the first stage reaction chamber.

12 Claims, 2 Drawing Figures

ALGAE BIOPOLYMER PRODUCTION

BACKGROUND OF THE INVENTION

This invention relates to the synthesis of algae biopolymers and more particularly to a method and apparatus for the enhancement of alga biopolymer production by nitrogen limitation.

The cultivation of microalgae to recover biopolymers as well as other products in the algal biomass is well known in the art. Such algae biopolymers are useful in various applications such as thickening agents for mobility control in waterflood oil recovery, as food additives, as flocculants useful in waste water treatment, soil conditioning, and as drilling mud extenders. Algae biopolymers may be synthesized by microalgae from the divisions Chlorophyta, Cyanophyta, and Rhodophyta. Genera within these divisions include: Chlorophyta—Chlorella, Ulva, Chlamydomonas, Scenedesmus, and Stichococcus; Cyanophyta—Anabaena; and Rhodophyta—Porphyridium. Particular algae species which may be employed in the synthesis of such biopolymers include: *Chlorella stigmataphora, Chlorella vulgaris, Chlorella pyrenoidosa, Chlamydomonas mexicana, Ulva lactuca, Scenedesmus obliquus, Scenedesmus braziliensis, Stichococcus bacillaris, Anabaena flos-aquae, Porphyridium aerugineum,* and *Porphyridium cruentum.*

Cultivation of the algae requires a nutrient medium containing nitrogen and other mineral nutrients and micronutrients, a source of assimilable carbon, illumination with light energy, and favorable conditions of temperature, pH, and salinity. Normally carbon dioxide is employed and this is required in the case of the obligate photoautotrophs which are capable of growth only by photosynthetically incorporating carbon dioxide. However, in the case of algae capable of photoheterotrophic growth, assimilable carbon may be provided by a preformed organic carbon source such as glucose, mannose, fructose, either alone or in combination with carbon dioxide.

Various processes for the cultivation of algae biomass and production of biopolymers are carried out in two stages, a first stage in which algae growth is initiated and a second stage in which biopolymer is carried to completion. Thus, U.S. Pat. No. 4,079,544 to Savins discloses a biopolymer synthesis procedure employing a culture medium having designated amounts of sodium nitrate and sodium glycerophosphate. In the first stage, the algae culture is subjected continuously to artificial illumination under conditions in which certain radiant energy parameters are controlled. In the second stage, artificial illumination is terminated and the culture is subjected to diurnal cycles of solar radiation and darkness provided by natural outdoor illumination. U.S. Pat. No. 4,078,332 to Savins also discloses a two-stage process for the synthesis of algae biopolymer employing diurnal cycles of solar radiation and darkness in the second stage as well as an apparatus which may be employed in implementing the process. In this procedure, the culture in the first stage is contacted with a mixture of carbon dioxide and air and irradiated with artificial illumination of an intensity and for a time to begin the synthesis of the algae biopolymer. The algae culture is also contacted with a mixture of carbon dioxide and air during the second stage in which biopolymer production is carried to conclusion.

U.S. Pat. No. 4,087,936 to Savins and Anderson discloses a two-stage process for the production of algae biopolymer employing a seed reactor and a main reactor. In the seed reactor, the algae culture is subjected to artificial illumination to initiate algae growth. At least a portion of the algae culture is then transferred from the seed reactor to the main reactor where it is subjected to artificial illumination to effect growth of the algae and synthesis of the algae biopolymer. In both stages a carbon dioxide-air mixture is employed and the linear gradient of the cumulative absorbed radiant energy is manipulated over an initial period of less than two days along with the cumulative absorbed moles of radiant energy quanta from the illumination and the ratio of these two parameters.

Yet another two-stage synthesis procedure in which a nitrogen deficiency is created to enhance biopolymer production is disclosed in U.S. Pat. No. 3,958,364 to Schenck et al. In this procedure a first culture tank is employed as a vegetative growth chamber and a second culture tank is employed as a polymer production chamber. In the first tank, the alga is cultivated in a nitrogen-containing nutrient medium sustaining exponential cell growth until a desired cell density is reached. Thereafter, approximately one-half of the culture volume is transferred from the first tank to the second tank. The first tank is then filled with fresh nutrient medium to its original volume and the second tank is filled with water. In the second tank, a nitrogen deficiency is created which enhances biopolymer production at the expense of cell growth. When the culture in the second tank reaches a desired optical density, it is then removed and the biopolymer recovered.

SUMMARY OF THE INVENTION

In accordance with the present invention there is provided a new and improved process for the synthesis of algae biopolymer wherein biopolymer production is enhanced by creating a nitrogen deficiency in the algae culture to shift from a growth phase favoring cell division to a senescent phase favoring biopolymer production. This improvement comprises carrying out the growth phase in a first stage operated in a continuous mode in which fresh nitrogen-containing nutrient medium is supplied to the culture medium to sustain exponential cell growth. Concomitantly with the supply of fresh nutrient medium to the first stage, a portion of the algae culture is transferred to a second stage. In this stage, the supply of nitrogen is limited to create a nitrogen deficiency in the culture medium which enhances biopolymer production.

In a preferred embodiment of the invention, the incident light energy applied to the first and second stages is controlled such that the illumination rate in the first stage is lower than in the second stage. In a further embodiment of the invention, variations in the first stage growth rate are minimized by maintaining the cell density in the first stage at a designated level. This is accomplished by monitoring the cell density in the first stage. Fresh nutrient medium is added to the first stage and algae culture transferred from the first stage to the second stage in response to an increase in the first stage cell density. Thus, as the cell density tends to increase above the desired level, the influx of fresh nutrient and the withdrawal of culture tend to maintain the cell density substantially constant.

In a further aspect of the invention there is provided a new and improved system for the production of algae biopolymer. This system comprises a first stage reaction chamber which is adapted to contain an algae culture and has inlet for the introduction of nutrient and an outlet for the withdrawal of culture. The chamber is equipped with suitable cell density sensing means which functions to generate a control function representative of the cell density. The system further comprises means for regulating the introduction of nutrient medium to the inlet and the withdrawal of culture from the outlet in response to the control function. There is further provided a plurality of second stage reaction chambers which are adapted to receive culture from the first stage reaction chamber. The first and second stage chambers are interconnected by means for sequentially transferring culture from the outlet of the first stage chamber to the second stage reaction chamber. Preferably the first stage reaction chamber comprises a thin layer reaction chamber having an interior spacing of 2 centimeters or less between opposed walls transparent to light energy.

DESCRIPTION OF THE SPECIFIC EMBODIMENTS

Figure 1:
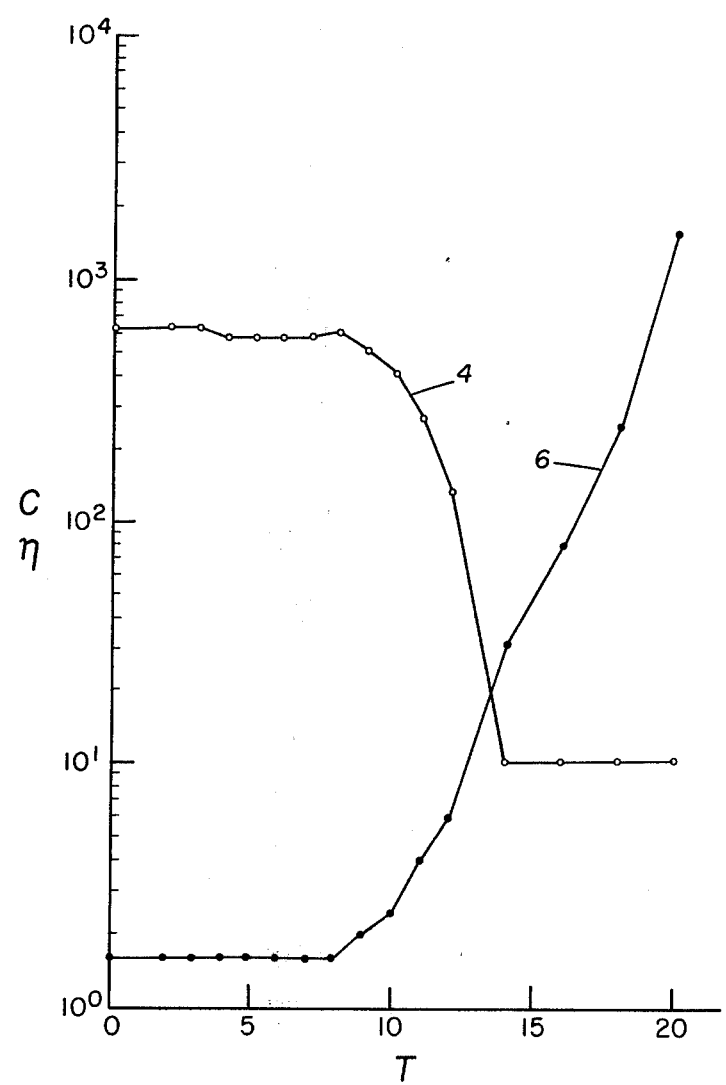
FIG. 1 is a graph showing the results of experimental work carried out regarding the present invention and illustrating the relationship between nitrogen concentration and viscosity of an algae culture with time.

In the cultivation of alga biomass, there is an inverse relationship between the rate of growth of the algae cells and the amount of biopolymer produced per cell. Thus, there is a competitive process between cell division and biopolymer production. A high growth rate results in a low polymer production rate and conversely polymer production may be enhanced by limiting the growth rate. As disclosed in the aforementioned patent to Schenck et al., the competitive processes may be utilized to advantage by first cultivating the algae in a nitrogen sufficient culture and then creating a nitrogen deficiency in the culture to increase polymer production.

This mechanism may be illustrated by reference to the photosynthetic conversion of carbon by the species *Porphyridium aerugineum* employed in the hereinafter described experimental work. There are two main points at which carbon is removed from the photosynthetic carbon reduction cycle, as 3-phosphoglyceric acid and fructose-6-phosphate. The points of removal are regulated by the inorganic nitrogen supplied to the culture medium. In the case of a nitrogen sufficiency, carbon is removed from the cycle as 3-phosphoglyceric acid which in turn is aminated directly to amino acids or which enters the tricarboxylic acid cycle and the products then transaminated to amino acids. The amino acids are converted to structural and regulatory proteins and new cells are made. When a nitrogen deficiency occurs, carbon is removed from the synthetic carbon reduction cycle as fructose-6-phosphate and converted to glucose-6-phosphate which in turn is converted to carbohydrates, in the case of *Porphyridium aerugineum*—floridean starch and anionic biopolymer.

In the present invention, nitrogen regulation of cell growth and biopolymer production is effected by culturing the algae in two series linked stages. The first stage is operated in a continuous culture mode in which fresh nitrogen-containing nutrient medium is supplied to the culture in an amount to sustain exponential cell growth. When a sufficiently high cell density is obtained, a portion of the algae culture is withdrawn from the first stage and transferred to the second stage where it is shifted to a batch mode of operation. As culture is withdrawn from the first stage, additional fresh nitrogen-containing nutrient medium is supplied to the first stage to sustain the continuous culture operation.

In the second stage, nitrogen is initially utilized in cell growth. However, as the nitrogen content of the culture becomes progressively lower, a nitrogen deficiency is created and the algae cells progressively shift from protein production to carbohydrate production. The cells ultimately enter into a phase of intense biopolymer production which is allowed to continue until the desired biopolymer concentration is reached. Thereafter, the culture is withdrawn from the second stage and treated to recover biopolymer by any suitable technique such as disclosed in the aforementioned patents to Savins.

In a preferred embodiment of the invention, the incident light energy to the first and second stages is controlled to provide a lower illumination rate in the first stage than in the second stage, thus increasing the photosynthetic capacity of the cells which is utilized in the second stage for greater biopolymer production. In this regard, the pigment concentration of the algae cells varies inversely with light intensity and directly with the availability of inorganic nitrogen. Thus, by growing the cells at a relatively low light intensity in the first stage with a sufficiency of nitrogen, relatively high pigment concentrations are achieved. With the cells thus adapted to a low light intensity and therefore of a high photon capture capacity, the cells when transferred to the second stage are forced to absorb additional light, thus increasing the rate of photosynthesis. In this manner, biopolymer production is additionally enhanced by employing the nitrogen starvation mechanism in combination with the increased photosynthetic capacity. Preferably, the ratio of the illumination rate during the second stage to the illumination rate during the first stage is at least 1.5. The illumination rate in the second stage may be increased further to provide a ratio of about 2. While even greater increases of illumination may be employed during the second stage, there seldom will be any corresponding benefit in increasing the second stage illumination rate by a factor greater than 2.

In the production of biopolymer by cultivation of the species *Porphyridium aerugineum*, it is preferred to provide illumination to the first stage at a rate within the range of 2.0 to 2.5 Einsteins per day per liter of culture. In the second stage, the illumination rate is increased to a level within the range of 3.0 to 4.5 Einsteins per day per liter. As noted in the aforementioned U.S. Pat. No. 4,079,544, biopolymer production by cultivation of the species *Porphyridium aerugineum is enhanced by employing illumination of an energy content predominantly in the region of* 600–700 nanometers. This phenomenon is employed to advantage in the second stage of the present invention by not only increasing the illumination rate of the incident light energy but also providing that its energy content is predominantly in the region of 600–700 nanometers. In the first stage in which the algae culture is in the growth phase, the incident light energy need not be enriched within the aforementioned spectrum range. Here illumination may be provided by relatively broad spectra light energy across the visible light range, approximately 400–750 nanometers.

It is further preferred in practicing the present invention to carry out the first stage continuous culture operation employing a thin film illuminator in which the thickness of the culture medium is 2 centimeters or less. As disclosed for example in U.S. Pat. No. 2,732,662 to Myers et al., the rate of algae growth can be significantly enhanced by culturing the algae in a relatively thin layer. This increase in growth rate is beneficial in carrying out the present invention. In addition, the use of a thin film illuminator allows for relatively uniform illumination throughout the algae culture. This is of particular significance since this provides for close regulation of the relative incident light intensity as applied to the algae culture during the first and second stages of the present invention. Also thin film illumination in the first stage enables illumination to be applied throughout the culture at a substantially constant rate, thus favoring the attainment of the steady state growth condition in the first phase as described hereinafter. Preferably, the thickness of the algae culture in the thin film illuminator is 1 centimeter or less. Although steady state growth kinetics are not of significance in the second stage operation, it is also desirable to employ a thin film illuminator in the second stage in order to provide for regulation of the relative incident light intensity as described above and to increase the energy available for photosynthetic conversion of carbon to biopolymer.

The nitrogen source necessary for cell growth may be provided by any suitable form of fixed nitrogen such as sodium, potassium metal or ammonium nitrates, other ammonium compounds, or urea. As noted previously, the assimilable carbon normally will be provided by carbon dioxide since most polymer producing algae are obligate photoautotrophs. A typical source of carbon dioxide is air enriched with about 2.5% to 5% carbon dioxide. Other mineral nutrients and micronutrients normally present in the nutrient medium include sulfates, phosphates, magnesium, manganese, zinc, calcium, cobalt, boron, and vitamin $B_{12}$. Optimum temperatures for algae growth normally will fall within the range of 18° to 25° C. and optimum pH within the range of 6 to 8. The salinity may vary from distilled water up to a total dissolved salts content of about 3 weight percent for certain marine species. For a more detailed description of the nutrient requirements and conditions for algae growth, reference is made to Burlew, J. S., Editor, "Algal Culture from Laboratory to Pilot Plant", Carnegie Institution of Washington Publication 600, Washington, D.C., and more particularly Part II thereof, "Conditions for Growth of Algae".

Experimental work relative to the present invention was carried out employing a culture of the species *Porphyridium aerugineum* (UTEX 755). *Porphyridium aerugineum* is a red algae of the division Rhodophyta. The growth of *Porphyridium aerugineum* for the production of biopolymer and nutrient medium suitable for its cultivation are described in U.S. Pat. No. 4,078,331 to Savins and Paul. In this experimental work, a modified nutrient medium containing the additives in the amounts and in the order of addition set forth in Table I was employed. Table II sets forth the content and additive concentrations of the PII trace metal mix added in an amount of 20 milliliters per liter subsequent to adjustment of the solution to a pH of 6.6 with hydrochloric acid. After addition of the nutrients and micronutrients, the medium was adjusted to a pH of 7.5 with sodium hydroxide and heat sterilized by autoclaving.

TABLE I

| | |
|---|---|
| $Na_2HPO_4$ | 228 mg/l |
| adjust pH to 6.6 with HCl | |
| PII trace metal mix | 20 ml/l |
| Vitamin $B_{12}$ | 7 ug/l |
| $NaNO_3$ | 884 mg/l |
| $MgSO_4 . 7H_2O$ | 200 mg/l |
| $CaCl_2 . 2H_2O$ | 73 mg/l |
| KCl | 60 mg/l |

TABLE II

| | |
|---|---|
| $H_3BO_3$ | 1140 mg/l |
| $MnCl_2 . 4H_2O$ | 144 mg/l |
| $ZnCl_2$ | 10.9 mg/l |
| $CoCl_2 . 6H_2O$ | 4.4 mg/l |
| $FeCl_3 . 6H_2O$ | 49 mg/l |
| $Na_2EDTA$ | 1000 mg/l |

Experimental work was carried out in a parallel plate illuminator having a 1-liter capacity with an internal dimension between the parallel glass plates of 0.5 centimeter. The parallel plate illuminator was operated as a reaction chamber in a chemostat mode in which fresh nutrient solution was added to the chamber and culture solution withdrawn at the same rate so that the volume of algae culture in the chamber remained constant. A peristaltic pump was employed to introduce fresh nutrient medium and withdraw spent culture from the chamber. The fresh nutrient solution was added to the chamber at a flow rate within the range of 0.3–0.5 dilutions per day. A mixture of air and 5% carbon dioxide was bubbled continuously through the chamber at a rate of 2.2 liters per minute and the culture was maintained at a temperature of 18° C.

In the continuous culture operation simulating the first stage of the present invention, the illumination rate of the incident light energy was adjusted at a level of 2.26 Einsteins per liter per day. Illumination was provided continuously by Sylvania "Cool White" fluorescent lamps. The fresh nutrient medium set forth in Tables I and II was provided to the reaction chamber at the aforementioned dilution rate of 0.3–0.5 dilutions per day and culture medium was withdrawn from the chamber at this same rate to maintain a constant volume. This first stage operation was continued for a period of 8 days. In this stage, the culture was maintained at a concentration of approximately ten million cells per milliliter. An exponential growth phase was sustained with biomass doublings averaging about 0.7 per day and ranging up to 1.5 per day. At the conclusion of the 8-day period, the culture was shifted to a batch mode operation simulating the second stage of the present invention by terminating the flow of fresh nutrient and withdrawal of culture and by increasing the illumination rate of the incident light energy to 4.34 Einsteins per day per liter. During the first and second stages, the nitrate concentration in the cell was monitored by nitrogen electrode. The stage 2 operation was continued for a period of 12 days. Within 6 days, after shifting from the first to the second stage, nitrate in the culture medium was substantially depleted and a period of intense polymer synthesis was underway. At the end of the stage 2 operation, the viscosity of the culture had increased to a level of about 1500 centipoises from a level of less than 2 centipoises at the end of the stage 1 operation.

Turning now to the drawings, FIG. 1 is a graph illustrating the relationship between nitrate concentration and culture viscosity with time during the first and second stages. In FIG. 1, curve 4 is a plot of the log of produced (column 5) by the absorbed quanta in Einsteins (column 2) and multiplying by 100.

TABLE III

| culture age (days) | $E_a$ (einsteins) | (kcal) | biopolymer (g/l) | (mol/l) | (kcal/l) | Y (mol/mol) | (kcal/kcal) |
|---|---|---|---|---|---|---|---|
| 9  | .12 | 4.49  | .06  | .0003 | .20  | .24  | 4.45 |
| 10 | .17 | 6.35  | .07  | .0004 | .27  | .23  | 4.25 |
| 11 | .22 | 8.22  | .10  | .0006 | .40  | .27  | 4.87 |
| 12 | .24 | 8.97  | .16  | .0008 | .54  | .33  | 6.02 |
| 14 | .61 | 22.80 | .55  | .0031 | 2.09 | .51  | 9.17 |
| 16 | .68 | 25.41 | .65  | .0036 | 2.42 | .33  | 9.52 |
| 18 | .71 | 26.54 | .90  | .0050 | 3.37 | .71  | 12.70 |
| 20 | .72 | 26.91 | 1.73 | .0096 | 6.46 | 1.34 | 24.00 |

TABLE IV

| culture age (days) | $E_a$ (einsteins) | (kcal) | biopolymer (g/l) | (mol/l) | (kcal/l) | Y (mol/mol) | (kcal/kcal) |
|---|---|---|---|---|---|---|---|
| 9  | .12  | 4.49   | .06  | .0003 | .20   | .25 | 4.45 |
| 10 | .29  | 10.84  | .13  | .0007 | .47   | .24 | 4.34 |
| 11 | .51  | 19.06  | .23  | .0013 | .87   | .25 | 4.56 |
| 12 | .76  | 28.41  | .39  | .0022 | 1.48  | .29 | 5.21 |
| 14 | 1.37 | 51.21  | .94  | .0052 | 3.50  | .38 | 6.83 |
| 16 | 2.05 | 76.63  | 1.59 | .0088 | 5.92  | .43 | 7.73 |
| 18 | 2.76 | 103.17 | 2.49 | .0138 | 9.29  | .50 | 9.00 |
| 20 | 3.48 | 130.08 | 4.22 | .0234 | 15.75 | .67 | 12.11 | nitrate concentration, C, in weight parts per million on the ordinate versus culture time, T, in days and curve 6 is a plot of the log of viscosity, $\eta$, in centipoises at a shear rate of 1.73 sec$^{-1}$ versus the culture time in days. As can be seen from examination of FIG. 1, upon termination of the first stage at 8 days, the nitrogen concentration decreased from a value of about 600 wppm nitrate to a final level of about 10 wppm nitrate. The amount of biopolymer produced as indicated by the solution viscosity increased rapidly as the nitrogen starvation set in.

The biopolymer production efficiency was calculated on two basis—(1) quantum yield expressed in terms of moles of biopolymer produced per mole quanta absorbed and (2) energy equivalent yield in terms of kilocalorie equivalents of biopolymer produced per kilocalorie of energy absorbed. Energy absorption in Einsteins was calculated at a wavelength of 550 nanometers equivalent to 37.38 kilocalories or 0.43 kilowatts. Molar equivalent weights of biopolymer were calculated using hexose ($C_6H_{12}O_6$) with 1 gram molecular weight of hexose (180 grams) equivalent to 673 kilocalories per mole.

The results of these calculations are set forth in Tables III and IV with Table III presenting the results in terms of incremental data and Table IV in terms of cumulative data. In each of Tables III and IV, the first column presents the culture age in days from the initiation of the first stage as time zero. Thus, a culture age of 9 days, for example, corresponds to the end of the first day of the second stage operation. The second and third columns present the light energy, $E_a$, absorbed in terms of Einsteins and kilocalories, respectively. The fourth, fifth, and sixth columns set forth the amount of biopolymer produced in terms of grams per liter, moles per liter, and kilocalories per liter, respectively. Columns 7 and 8 give the efficiency, Y, of biopolymer production expressed as percent yield on a quantum conversion basis and an energy conversion basis, respectively. Thus, the data presented in column 7, for example, is arrived at by dividing the moles per liter of biopolymer In Table IV, the biopolymer production efficiencies set forth in columns 7 and 8 are cumulative average values.

The growth kinetics in the first stage continuous culture operation may be expressed by the relationship:

$$N_1 = N_0 e^{(\beta - D)t} \quad (1)$$

wherein:
$N_0$ is the cell concentration in cells per unit volume at time zero,
$N_1$ is the cell concentration in cells per unit volume at the end of time, t,
$\beta$ is the growth constant per unit time,
D is the washout rate equivalent to the dilution rate in volumes per unit time, and
t is elapsed time.

From an examination of equation (1), it can be seen that where the growth rate and washout rate are equal ($\beta - D = 0$), a steady-state growth situation is arrived at in which there is no change in biomass. Ideally, the rate of cell division remains constant and exactly compensates for the culture medium withdrawn from the first stage and the fresh nutrient medium supplied thereto. Where $\beta$ and D are unequal, transient state growth obtains in which the cell division rate oscillates as new nutrient medium is added and culture withdrawn.

In a preferred embodiment of the invention, the first stage is operated in a mode approaching the steady-state growth condition in which oscillations in the cell division rate are minimized. This is accomplished by monitoring the cell density in the first stage and adding fresh nutrient medium and concomitantly withdrawing culture medium from the first stage as the cell density starts to increase above a designated level. By this technique, the cell density is maintained substantially constant to approach the steady-state growth condition.

Figure 2:
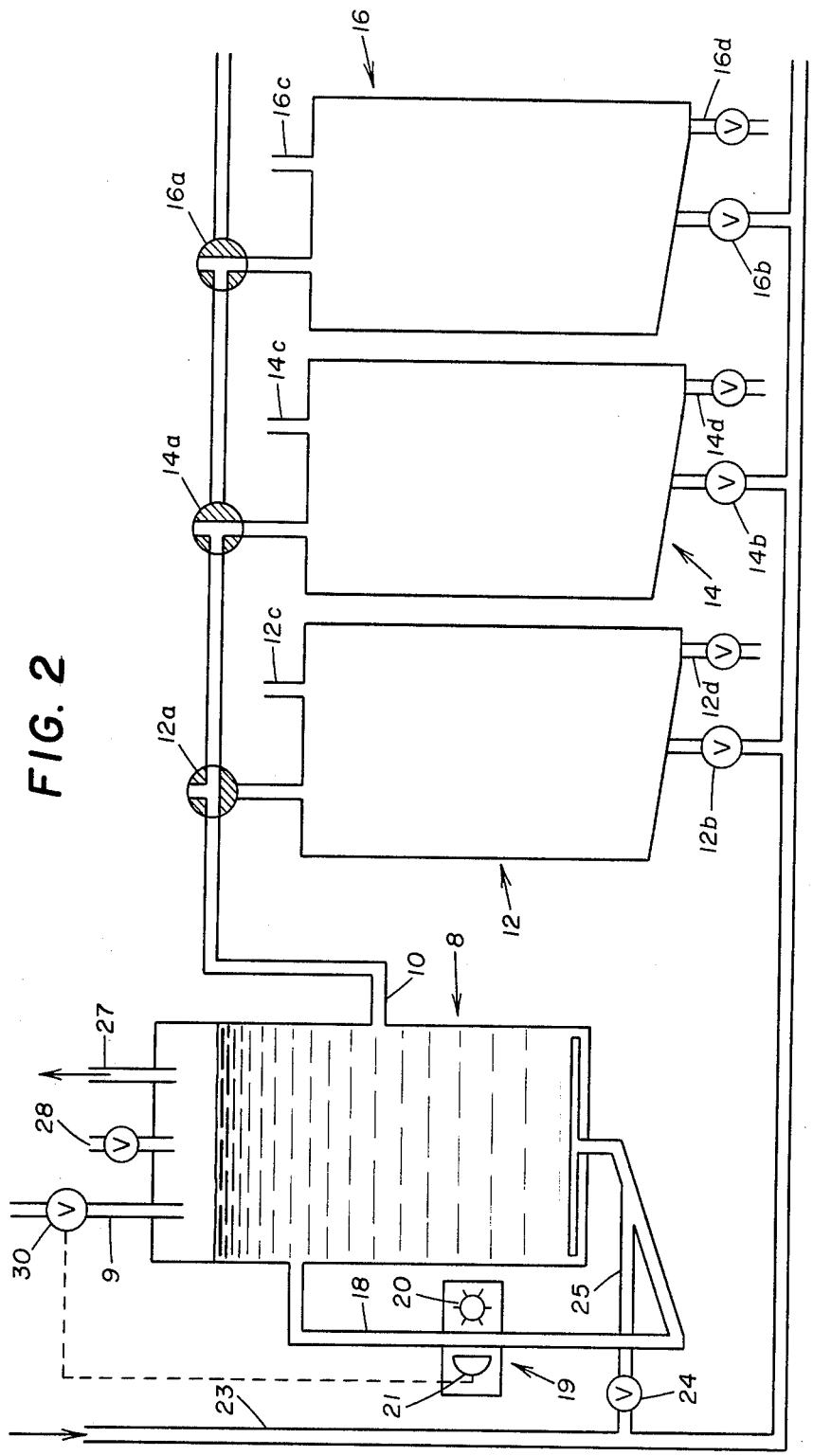
FIG. 2 is a schematic illustration of a system for producing algae biopolymer in accordance with the present invention.

Referring again to the drawings, FIG. 2 is a schematic illustration of a system which may be employed to synthesize alga biopolymer in accordance with the present invention. As shown in FIG. 2, the system comprises a first stage reaction chamber 8 provided with an inlet 9 for the introduction of fresh nutrient and an outlet 10 for the withdrawal of culture medium which is then supplied sequentially to a plurality of second stage reaction chambers 12, 14, and 16. The chamber 8 is equipped with a cell density sensing means which in the embodiment shown comprises a standpipe 18 and a sensing unit 19 comprising a light source 20, and a photoelectric cell 21. A mixture of carbon dioxide and air is supplied to the chamber from a source (not shown) via line 23 through a flow control valve 24 and line 25 in fluid communication with the standpipe. Thus, the supply of gas through line 25 functions to aspirate culture medium through the standpipe so that there is a continuous flow therethrough of culture medium of a density representative of the density within the chamber. Effluent gas is withdrawn from the chamber through an exhaust port 27. The chamber is also equipped with an inoculation port 28.

The inlet port 9 is equipped with a solenoid valve 30 under the control of the photoelectric cell. In initiating the first stage operation, the chamber 8 is filled with nutrient medium and inoculated with the microalgae. The chamber is illuminated with a light source (not shown) and the first stage is operated initially in a batch mode until the cell density reaches a desired population. Thereafter, as the cell population tends to increase above the desired level, the light input to the photoelectric cell is diminished. The corresponding signal from the photoelectric cell acts through suitable means such as a current or voltage actuated relay (not shown) to operate to open solenoid valve 30. As fresh nutrient medium is introduced into the first stage reaction chamber, culture is forced via outlet 10 to the second stage which as shown on the drawing preferably comprises a plurality of chambers. Ideally, the number of second stage reaction chambers is at least equal to the product of the flow rate in second stage chamber volumes from outlet 10 and the residence time in the second stage required for the desired polymer production. Thus, if the output from the first stage chamber is sufficient to fill one second stage chamber daily and a second stage residence time of 6 days is desired, at least 6 second stage chambers should be provided.

The culture medium is transferred sequentially to the second stage reaction chambers by any suitable means. In the embodiment shown, the chambers 12, 14, and 16 are provided with inlets controlled by 3-way, 2-position valves 12a, 14a, and 16a, respectively. The inlet valves are controlled by suitable means so that the culture effluent from the chamber 8 is supplied in sequence to each of the chambers 12, 14, and 16. Thus as illustrated in the drawing, chamber 12 has been filled with the culture medium and is operating in a batch mode for biopolymer production. Culture effluent from outlet 10 now flows through valve 14a to chamber 14 and when it is filled to capacity, valve 14a is switched to the line position to allow culture to flow into the third chamber 16. The valves 12a, 14a, and 16a may be operated by any suitable means. For example, they may be operated by a sequential timer or by liquid level indicators within the chambers 12, 14, and 16. During the biopolymer production stage, carbon dioxide enriched air is passed to the second stage chambers by flow regulating valves 12b, 14b, and 16b and withdrawn through exhaust ports 12c, 14c, and 16c. At the conclusion of the desired residence time, the culture is removed from the second stage chambers via outlets 12d, 14d, and 16d and then processed by any suitable technique for the recovery of biopolymer.

It will be recognized that the system shown in FIG. 2 is exemplary only and that any suitable means may be employed for supplying fresh nutrient to the first stage reaction chamber and sequentially transferring culture to the second stage reaction chambers. For example, while a gravity feed system is illustrated, fluid transfer may be effected through the use of pumps operated by suitable control systems. Similarly, the cell density monitoring means may take other forms than the photoelectric device illustrated. For example, an electronic particle counter may be employed to obtain instantaneous readings of cell mass in the first stage reaction chamber and control the flow of fresh nutrient to the chamber.

I claim:

1. In a process for the production of biopolymer by cultivation of algae in an aqueous culture in the presence of assimilable carbon and incident light energy wherein biopolymer production is enhanced by creating a nitrogen deficiency in said culture to shift from a growth phase favoring cell division to a senescent phase favoring biopolymer production, the improvement comprising:
    (a) carrying out said growth phase in a first stage operated in a continuous mode in which fresh nitrogen-containing nutrient medium is supplied to said culture to sustain exponential cell growth, and
    (b) concomitantly with the supply of fresh nutrient medium to said first stage, transferring a portion of said culture to a second stage which is separate from said first stage and in which assimilable carbon is supplied to said culture while the supply of nitrogen is limited to create a nitrogen deficiency in said second stage to enhance biopolymer production while continuing to supply fresh nitrogen-containing nutrient medium to said first stage to continue said growth phase.

2. The method of claim 1 wherein the illumination rate of incident light energy is lower in said first stage than in said second stage.

3. The method of claim 2 wherein the ratio of the illumination rate during said second stage to the illumination rate during said first stage is at least 1.5.

4. The method of claim 1 wherein said culture during said first stage has a thickness of 2 centimeters or less.

5. The method of claim 1 wherein said culture during said first stage has a thickness of 1 centimeter or less.

6. The method of claim 1 further comprising the step of monitoring the cell density in said first stage and adding fresh nutrient medium to said first stage and transferring culture from said first stage to said second stage in response to an increase in cell density in said first stage above a designated level to maintain said cell density substantially at said designated level.

7. The method of claim 1 wherein step (b) is implemented by successively transferring culture from said first stage to a plurality of reaction zones in said second stage whereby biopolymer production occurs in each of said second stage reaction zones simultaneously with cell growth in said first stage.

8. The method of claim 1 wherein biopolymer is produced by cultivation of *Porphyridium aerugineum*.

9. The method of claim 8 wherein the illumination rate of incident light energy is within the range of 2.0 to 2.5 Einsteins per day per liter during said first stage and within the range of 3.0 to 4.5 Einsteins per day per liter during said second stage.

10. The method of claim 9 wherein the incident light energy during said second stage has an energy content predominantly in the region of 600 to 700 nanometers.

11. In a system for the production of alga biopolymer, the combination comprising:

a first stage reaction chamber adapted to contain a culture of algae cells and having an inlet for the introduction of a nutrient medium to said chamber and an outlet for the withdrawal of culture therefrom, means for sensing the cell density in said chamber and generating a control function representative thereof, means responsive to said control function for regulating the introduction of nutrient medium to said inlet and the withdrawal of culture from said outlet, a plurality of second stage reaction chambers adapted to receive culture from said first stage reaction chamber, and means for sequentially transferring culture from the outlet of said first stage reaction chamber to said second stage reaction chambers.

12. The system of claim 11 wherein said first stage chamber is a thin layer reaction chamber having an interior spacing of 2 centimeters or less between opposed walls which are transparent to light energy.

* * * * *

UNITED STATES PATENT AND TRADEMARK OFFICE
CERTIFICATE OF CORRECTION

PATENT NO. : 4,236,349
DATED : December 2, 1980
INVENTOR(S) : Joseph S. RAMUS

It is certified that error appears in the above–identified patent and that said Letters Patent are hereby corrected as shown below:

Column 1, lines 19-21, should read as follows, with the underlined portions italicized:

"phyta -- *Chlorella*, *Ulva*, *Chlamydomonas*, *Scenedesmus*, and *Stichococcus*; Cyanophyta -- *Anabaena*; and Rhodophyta -- *Porphyridium*. Particular algae species"

Column 4, lines 56-58, the following should not be italicized:

"is enhanced by employing illumination of an energy content predominantly in the region of"

Signed and Sealed this

Seventh Day of April 1981

[SEAL]

Attest:

RENE D. TEGTMEYER

Attesting Officer  Acting Commissioner of Patents and Trademarks